(12) United States Patent
Parthasaradhi Reddy et al.

(10) Patent No.: US 8,389,531 B2
(45) Date of Patent: Mar. 5, 2013

(54) PROCESS FOR ERLOTINIB HYDROCHLORIDE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Thungathurthy Srinivasa Rao, Hyderabad (IN)

(73) Assignee: Hetero Drugs Limited (IN)

( * ) Notice: Subject to any disclaimer, the term of this patent is extended or adjusted under 35 U.S.C. 154(b) by 216 days.

(21) Appl. No.: 11/994,613

(22) PCT Filed: Jul. 11, 2007

(86) PCT No.: PCT/IN2007/000288
§ 371 (c)(1),
(2), (4) Date: Jan. 3, 2008

(87) PCT Pub. No.: WO2009/007984
PCT Pub. Date: Jan. 15, 2009

(65) Prior Publication Data
US 2010/0130741 A1    May 27, 2010

(51) Int. Cl.
*A01N 43/54* (2006.01)
*A61K 31/517* (2006.01)
*C07D 239/72* (2006.01)

(52) U.S. Cl. .................. 514/266.31; 544/293

(58) Field of Classification Search ............. 514/266.31; 544/293
See application file for complete search history.

(56) References Cited

U.S. PATENT DOCUMENTS 4,026,894 A * 5/1977 Winn et al. .................. 544/291
5,747,498 A    5/1998 Schnur et al.
2008/0058355 A1   3/2008 Westheim
2008/0167327 A1   7/2008 Westheim
2008/0318950 A1  12/2008 Ahn et al.

FOREIGN PATENT DOCUMENTS

| EP | 1044969 A2 | 10/2000 |
| WO | 9955683 A1 | 11/1999 |
| WO | 0134574 A1 | 5/2001 |
| WO | 2007060691 A2 | 5/2007 |
| WO | 2007117607 A2 | 10/2007 |
| WO | 2007138613 A2 | 12/2007 |
| WO | 2008122776 A2 | 10/2008 |

OTHER PUBLICATIONS

PCT Noification of Transmittal of the International Search Report and the Written Opinion of the International Searching Authority or the Declaration, Done by Maria Henczi on Jul. 20, 2009.
PCT Written Opinion of the International Searching Authority, Done by Maria Henczi on Jul. 20, 2009.
PCT Noification of Transmittal of the International Search Report and the Written Opinion of the International Searching Authority or the Declaration, (May 12, 2009).
PCT Written Opinion of the International Searching Authority, (May 12, 2009).
www.lclabs.com/PRODFILE/D-F/E-4007.php4.

* cited by examiner

Primary Examiner — Paul V. Ward
(74) Attorney, Agent, or Firm — Cantor Colburn LLP

(57) ABSTRACT

The present invention provides an improved and commercially viable process for preparation of erlotinib substantially free of N-methoxyethyl impurity, namely N-[(3-ethynylphenyl)-(2-methoxyethyl)]-6,7-bis(2-methoxyethoxy)-4-quinazolinamine, and its pharmaceutically acceptable acid addition salts thereof in high purity and in high yield. According to the present invention, erlotinib or a pharmaceutically acceptable acid addition salt of erlotinib substantially free of N-methoxyethyl impurity is prepared by isolating erlotinib or a pharmaceutically acceptable salt of erlotinib from a solvent medium comprising dimethyl sulfoxide and an alcoholic solvent.

24 Claims, No Drawings

PROCESS FOR ERLOTINIB HYDROCHLORIDE

FIELD OF THE INVENTION

The present invention provides an improved and commercially viable process for preparation of erlotinib substantially free of N-methoxyethyl impurity, namely N-[(3-ethynylphenyl)-(2-methoxyethyl)]-6,7-bis(2-methoxy ethoxy)-4-quinazolinamine, and its pharmaceutically acceptable acid addition salts thereof in high purity and in high yield.

BACKGROUND OF THE INVENTION

U.S. Pat. No. 5,747,498 discloses 4-(substituted phenylamino) quinazoline derivatives, processes for their preparation, pharmaceutical compositions in which they are present and a method of use thereof. These compounds are Tyrosine Kinase Inhibitors and are useful in the treatment of hyperproliferative diseases, such as cancers, in mammals. Among them, erlotinib hydrochloride, chemically N-(3-ethynylphenyl)-6,7-bis(2-methoxy ethoxy)-4-quinazolinamine hydrochloride is a selective inhibitor of the erbB family of oncogenic and protooncogenic protein tyrosine kinases, such as epidermal growth factor receptor (EGFR), and is useful for the treatment of proliferative disorders, such as cancers, particularly non small cell lung cancer, pancreatic cancer, ovarian cancer, breast cancer, glioma, head cancer or neck cancer. Erlotinib is represented by the following structure:

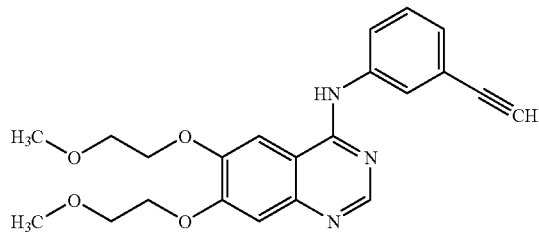 [SMILES: C#Cc1cccc(Nc2ncnc3cc(OCCOC)c(OCCOC)cc23)c1]

Various processes for the preparation of erlotinib and related compounds are disclosed in U.S. Pat. No. 5,747,498, European Patent Application No. 1044969 A2, PCT Patent Publication No. WO 01/34574 A1 and PCT Patent Publication No. WO 2007/060691 A2.

As per the process described in U.S. Pat. No. 5,747,498 (hereinafter "the '498 patent"), erlotinib hydrochloride can be prepared by the reaction of 4-chloro-6,7-bis-(2-methoxy-ethoxy)-quinazoline, obtained by reaction of 6,7-bis(2-methoxy-ethoxy)-quinazolone with oxalylchloride in a solvent system containing chloroform and dimethylformamide, with 3-ethynylaniline or its hydrochloride salt in a solvent such as a ($C_1$-$C_6$)-alcohol, dimethylformamide, N-methylpyrrolidin-2-one, chloroform, acetonitrile, tetrahydrofuran, 1,4-dioxane, pyridine or another aprotic solvent, preferably isopropyl alcohol; in the presence or absence of a base, preferably an alkali or alkaline earth metal carbonate or hydroxide or a tertiary amine base, such as pyridine, 2,6-lutidine, collidine, N-methyl-morpholine, triethylamine, 4-dimethylamino-pyridine or N,N-dimethylaniline; at a temperature from about ambient to about the reflux temperature of the solvent, preferably from about 35° C. to about reflux; under an inert atmosphere such as dry nitrogen. The crude erlotinib hydrochloride (residue) obtained is then basified with saturated aqueous $NaHCO_3$ in the presence of methanol and chloroform followed by flash chromatography on silica using 30% acetone in hexane to afford erlotinib free base, which is further treated with hydrochloric acid in the presence of diethyl ether and chloroform to give erlotinib hydrochloride.

Erlotinib hydrochloride obtained by the process described in the '498 patent is not satisfactory from a purity point of view. The yield of erlotinib hydrochloride obtained according to the process described in the '498 patent is very poor and the process involves column chromatographic purifications. Methods involving column chromatographic purifications cannot be used for large-scale operations, thereby making the process commercially not viable.

According to European Patent No. 1044969, erlotinib hydrochloride is prepared, either by (i) reacting 6,7-bis(2-methoxyethoxy)-N43-[(trimethylsilyl)ethynyl]phenyl-4-quinazolinamine monohydrochloride, obtained by the reaction of 4-chloro-6,7-bis(2-methoxyethoxy)quinazoline with a solution of 3-[(trimethylsilyl)ethynyl]aniline in 2-propanol at reflux, with tetra-n-butylammonium fluoride in an aprotic solvent such as tetrahydrofuran, diethyl ether, dimethoxyethane, toluene, dichloromethane and chloroform, and then treating the reaction mass with concentrated hydrochloric acid in 2-propanol; or (ii) reacting 4-[3-[[6,7-bis(2-methoxyethoxy)-4-quinazolinyl]amino]phenyl]-2-methyl-3-butyn-2-ol or its monohydrochloride salt, obtained by the reaction of 4-chloro-6,7-bis(2-methoxyethoxy)quinazoline with 4-(3-aminophenyl)-2-methyl-3-butyn-2-ol in acetonitrile at reflux, with an alkali-metal or alkaline-metal hydroxide such as sodium hydroxide, lithium hydroxide, cesium hydroxide, calcium hydroxide, magnesium hydroxide and potassium hydroxide, in an alcoholic solvent such as 1-butanol, 2-butanol and 2-propanol, and then treating the reaction mass with concentrated hydrochloric acid in an alcoholic solvent.

The synthetic routes of erlotinib hydrochloride as described in European Patent No. 1044969 involve lengthy processes and expensive raw materials, and the yields obtained in these routes are not satisfactory, thereby making the processes commercially not viable.

PCT Patent Publication No. WO 99/55683 discloses erlotinib mesylate anhydrate and hydrate polymorphic forms, their method of preparation and pharmaceutical compositions containing thereof.

PCT Patent Publication No. WO 01/34574 A1 describes a process for the preparation of erlotinib hydrochloride in crystalline polymorphic form B, which comprises: a) reacting 4-chloro-6,7-bis(2-methoxyethoxy)quinazoline, obtained by reaction of 4-hydroxy-6,7-bis(2-methoxyethoxy)quinazoline with thionyl chloride in a solvent mixture of methylene chloride and dimethylformamide, with 3-ethynylaniline, prepared by reaction of 4-(3-aminophenyl)-2-methyl-3-butyn-2-ol with a suspension of sodium hydroxide (or potassium hydroxide, or a combination) in toluene with heating, to give N-(3-ethynylphenyl)-6,7-bis(2-methoxyethoxy)-4-quinazolinamine hydrochloride; b) recrystallizing the N-(3-ethynylphenyl)-6,7-bis(2-methoxyethoxy)-4-quinazolinamine hydrochloride, in a solvent comprising alcohol and water, into the polymorphic form B.

PCT Patent Publication No. WO 2007/060691 A2 describes an improved process for the preparation of erlotinib hydrochloride, which comprises: i) reacting 6,7-dimethoxy-4-(3H)-quinazolinone with aqueous hydrobromic acid or pyridine hydrochloride at an elevated temperature to get a hydrobromide or hydrochloride salt of 6,7-dihydroxy-4-(3H)-quinazolinone which on neutralization with a base gives 6,7-dihydroxy-4-(3H)-quinazolinone; ii) acylating the dihydroxy compound using an acylating agent at a temperature in the range of 20-150° C. and in the presence of a catalyst to give 6,7-diacetoxy-4-(3H)-quinazolinone; iii) reacting the diacetoxy compound with oxalyl chloride at a temperature of 10-100° C. to give 4-chloro-6,7-diacetoxy-quinazoline; iv) condensing the reaction mass containing the chloro compound with 3-ethynylaniline in an organic solvent selected from chloroform, methylene chloride, acetonitrile, isopropyl alcohol, toluene, tetrahydrofuran, dioxane, cyclohexane and dimethylformamide, at a temperature of 10-100° C. to give N-(3-ethynylphenyl)-6,7-diacetoxy-4-quinazolinamine hydrochloride which on further treatment with a base such as aqueous sodium or potassium hydroxide, or aqueous ammonia solution in alcohols at a temperature of 20-60° C. gives N-(3-ethynylphenyl)-6,7-hydroxy-4-quinazolinamine; v) reacting the N-(3-ethynylphenyl)-6,7-hydroxy-4-quinazolinamine with 2-halo-ethylmethyl ether in the presence of a base at a temperature of 25-100° C. to give crude erlotinib base; vi) recrystallizing the crude erlotinib base from different solvents like ethyl acetate, acetonitrile, isopropyl alcohol, methanol, ethanol, acetone, methyl ethyl ketone, water or a mixture thereof to give pure erlotinib base; vii) reacting pure erlotinib base by dissolving or suspending in an organic solvent or water or a mixture thereof with aqueous hydrochloric acid or hydrogen chloride gas dissolved in an organic solvent selected from chloroform, toluene, ethanol, methanol, isopropyl alcohol, acetone, methyl ethyl ketone, acetonitrile, ethyl acetate, dimethylformamide, dimethyl ether, diethyl ether and tetrahydrofuran to give erlotinib hydrochloride.

The synthetic route of erlotinib hydrochloride described in PCT Patent Publication No. WO 2007/060691 A2 involves a lengthy process, and the yields obtained in this route are very low.

Erlotinib obtained by the processes described in the art is not satisfactory from a purity point of view. We have repeated the erlotinib synthetic procedures as described in the prior art mentioned above and found that relatively large amounts of impurities were obtained along with erlotinib. Among these impurities, the N-methoxyethyl impurity, namely N-[(3-ethynylphenyl)-(2-methoxyethyl)]-6,7-bis(2-methoxyethoxy)-4-quinazolinamine, of formula I:

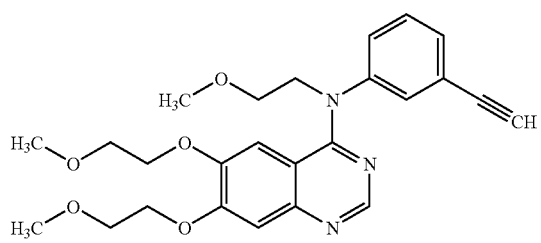

I was identified and isolated. In a specific run, we have found that erlotinib prepared by the above procedures contained about above 0.15% of the N-methoxyethyl impurity at about 1.1 Relative Retention Time (RRT) measured by High Performance Liquid Chromatography (HPLC), which could not be eliminated by re-crystallization, hence the only way to purify erlotinib was by column chromatography.

However, a need still remains for an improved and commercially viable process of preparing pure erlotinib hydrochloride that should solve the aforesaid problems associated with processes described in the prior art, which will be suitable for large-scale preparation, in terms of simplicity, chemical yield and purity of the product.

Extensive experimentation has been carried out by the present inventors to find the way to eliminate this N-methoxyethyl impurity. As a result, it has been found that the N-methoxyethyl impurity formed in the preparation of the erlotinib hydrochloride can be reduced or avoided by isolating erlotinib hydrochloride from a solvent medium comprising dimethyl sulfoxide and an alcoholic solvent in high purity and in high yield.

The object of the present invention is to provide an improved and commercially viable process for preparation of erlotinib substantially free of N-methoxyethyl impurity, namely N-[(3-ethynylphenyl)-(2-methoxyethyl)]-6,7-bis(2-methoxy ethoxy)-4-quinazolinamine, and its pharmaceutically acceptable acid addition salts thereof in high purity and in high yield.

Another object of the present invention is to provide erlotinib substantially free of N-methoxyethyl impurity, namely N-[(3-ethynylphenyl)-(2-methoxyethyl)]-6,7-bis(2-methoxyethoxy)-4-quinazolinamine, and its pharmaceutically acceptable acid addition salts thereof.

DETAILED DESCRIPTION OF THE INVENTION

According to one aspect of the present invention, there is provided erlotinib substantially free of N-methoxyethyl impurity, namely N-[(3-ethynylphenyl)-(2-methoxyethyl)]-6,7-bis(2-methoxyethoxy)-4-quinazolinamine, and its pharmaceutically acceptable acid addition salts thereof.

Preferable pharmaceutically acceptable acid addition salts of erlotinib, include but are not limited to, salts which are obtained from hydrochloric acid, hydrobromic acid, hydroiodic acid, methanesulfonic acid and benzenesulfonic acid, with the more preferable salt being erlotinib hydrochloride.

According to another aspect of the present invention, there is provided a process for preparation of erlotinib substantially free of N-methoxyethyl impurity, namely N-[(3-ethynylphenyl)-(2-methoxy ethyl)]-6,7-bis(2-methoxyethoxy)-4-quinazolinamine or a pharmaceutically acceptable salt thereof, which comprises isolating erlotinib or a pharmaceutically acceptable salt of erlotinib from a solvent medium comprising dimethyl sulfoxide and an alcoholic solvent.

Preferable alcoholic solvent include methanol, ethanol, isopropanol, tert-butanol, amyl alcohol, isoamyl alcohol, tert-amyl alcohol, or a mixture thereof, a more preferable alcoholic solvent is methanol or ethanol, and the most preferable alcoholic solvent is methanol.

The process of the invention may be carried out by a) reacting 4-chloro-6,7-bis-(2-methoxyethoxy)-quinazoline with 3-ethynylaniline or its hydrochloride salt in a solvent medium comprising dimethylsulfoxide and an alcoholic solvent in the presence or absence of a base; and b) isolating erlotinib as free base or a pharmaceutical acceptable acid addition salt substantially free of N-methoxyethyl impurity.

The reaction in step (a) may be carried out between about 60° C. and reflux temperature of the solvent medium used, preferably carried out between 65° C. and reflux temperature of the solvent medium used, and more preferably carried out between about 70° C. and reflux temperature of the solvent medium used.

As used herein, "reflux temperature" means the temperature at which the solvent or solvent system refluxes or boils at atmospheric pressure.

Erlotinib free base substantially free of N-methoxyethyl impurity is obtained as a product when the reaction is carried out in the presence of a base in step (a) followed by isolation of the compound obtained in step (b).

Preferably the base used in step (a) is an alkali or alkaline earth metal carbonate or hydroxide or a tertiary amine base, such as pyridine, 2,6-lutidine, collidine, N-methyl-morpholine, triethylamine, 4-dimethylamino-pyridine or N,N-dimethylaniline.

Preferably the reaction in step (a) is carried out in the absence of a base. Erlotinib hydrochloride substantially free of N-methoxyethyl impurity is obtained as a product when the reaction is carried out in the absence of a base in step (a) followed by isolation of the compound obtained in step (b).

If required, the erlotinib free base or hydrochloride salt obtained in step (a) may be converted into pharmaceutically acceptable acid addition salts by conventional methods.

Isolation of the erlotinib free base or a pharmaceutically acceptable acid addition salt of erlotinib substantially free of N-methoxyethyl impurity obtained in step (b) may be carried out by methods usually known in the art such as cooling, partial removal of the solvent from the solution, addition of precipitating solvent or a combination thereof.

Pharmaceutically acceptable acid addition salts of erlotinib are formed with appropriate organic or inorganic acids by methods known in the art.

Preferable pharmaceutically acceptable acid addition salts of erlotinib, include but are not limited to, salts obtained from hydrochloric acid, hydrobromic acid, hydroiodic acid, methanesulfonic acid and benzenesulfonic acid, with the more preferable salt being erlotinib hydrochloride.

4-Chloro-6,7-bis-(2-methoxyethoxy)-quinazoline and 3-ethynylaniline can be used as starting materials and may be obtained by processes described in the art, for example by the processes described in U.S. Pat. No. 5,747,498.

The process of the invention may also be carried out by dissolving crude erlotinib free base in a solvent medium comprising dimethylsulfoxide and an alcoholic solvent to form a clear solution, adding an acid to the solution, and collecting the precipitated solid to obtain an erlotinib pharmaceutically acceptable acid addition salt substantially free of N-methoxyethyl impurity.

Crude erlotinib free base used as the starting material may be obtained by processes described in the art, for example by the processes described in U.S. Pat. No. 5,747,498.

The precipitated erlotinib pharmaceutically acceptable acid addition salt substantially free of N-methoxyethyl impurity is collected by filtration or centrifugation.

The acid used in the above reaction is an organic or inorganic acid. Preferable acids are hydrochloric acid, hydrobromic acid, hydroiodic acid, methanesulfonic acid and benzenesulfonic acid, with the more preferable acid being hydrochloric acid. Hydrochloric acid used may be in the form of aqueous hydrochloric acid or in the form of hydrogen chloride gas or hydrogen chloride dissolved in an organic solvent. The organic solvent used for dissolving hydrogen chloride gas or hydrogen chloride is selected from the group consisting of ethanol, methanol, isopropyl alcohol, ethyl acetate, diethyl ether, dimethyl ether and acetone.

The process of the invention may also be carried out by dissolving or suspending crude erlotinib pharmaceutically acceptable acid addition salt in a solvent medium comprising dimethylsulfoxide and an alcoholic solvent, and isolating the erlotinib pharmaceutically acceptable acid addition salt substantially free of N-methoxyethyl impurity.

The crude erlotinib pharmaceutically acceptable acid addition salt used as the starting material may be obtained by processes described in the art, for example by the processes described in U.S. Pat. No. 5,747,498.

Isolation of an erlotinib pharmaceutically acceptable acid addition salt substantially free of N-methoxyethyl impurity may be carried out by methods usually known in the art such as cooling, partial removal of the solvent from the solution, addition of precipitating solvent or a combination thereof.

The preferable alcoholic solvent is methanol, ethanol, isopropanol, tert-butanol, amyl alcohol, isoamyl alcohol, tert-amyl alcohol, or a mixture thereof, a more preferable alcoholic solvent is methanol or ethanol, and the most preferable alcoholic solvent is methanol.

Preferable pharmaceutically acceptable acid addition salts of erlotinib are obtained from hydrochloric acid, hydrobromic acid, hydroiodic acid, methanesulfonic acid and benzenesulfonic acid, with the more preferable salt being erlotinib hydrochloride.

The purity (measured by 'HPLC) of the product obtained according to the present invention is preferably about above 99.5%, more preferably about above 99.7% and still more preferably about above 99.9%.

The term "erlotinib or pharmaceutically acceptable acid addition salts of erlotinib substantially free of N-methoxyethyl impurity" refers to the erlotinib or pharmaceutically acceptable acid addition salts of erlotinib having the content of N-methoxyethyl impurity in less than about 0.1% by weight, preferably less than about 0.05% by weight and still more preferably having no traces of the N-methoxyethyl impurity.

The terms "crude erlotinib" or "crude erlotinib hydrochloride" in the specification refers to erlotinib or erlotinib hydrochloride having the content of N-methoxyethyl impurity in more than about 0.1% by weight.

HPLC Method Used in the Specification is Provided Below:

| | |
|---|---|
| Column: | HYPERSIL BDS-C18, 150 × 4.6 mm 5 μm |
| Flow rate: | 1.0 ml/min |
| Temperature: | Ambient |
| Detector: | 247 nm |
| Mobile Phase: | Sol-A: - BUFFER |
| | Sol-B: - WATER:CH$_3$CN (5:95) |
| Buffer: | Dissolve 0.77 g of Ammonium acetate in 1000 mL of distilled water and adjust pH = 4.0 with acetic acid. |
| Sample Preparation: | Sol-A:Sol-B (1:1) |
| Final Concentration: | 0.5 mg/mL |
| Run Time: | 45 min |
| Injection volume: | 20 μL |

The following examples are given for the purpose of illustrating the present invention and should not be considered as limiting the scope or spirit of the invention.

REFERENCE EXAMPLES

Reference Example 1

6,7-Bis(2-methoxy-ethoxy)-quinazolone (68 gm), chloroform (1360 ml) and dimethylformamide (7.5 ml) are taken in a reaction flask at 25-30° C. and stirring begun. To the contents is added oxalyl chloride (120 ml) at 25-30° C. slowly for 30 minutes, which is then heated to reflux for 1 hour 30 minutes. The solvent is distilled at 55-60° C. under vacuum, diisopropyl ether (560 ml) is added, cooled to 25-30° C. and then stirred for 30 minutes. The compound is filtered and washed with diisopropyl ether (100 ml). The compound is added to chloroform (1000 ml), the chloroform is washed two times with 8% NaHCO$_3$ solution (each time 680 ml) and the resulting organic layer is washed with water (500 ml), the organic layer is dried over sodium sulfate and the solvent is distilled under a vacuum at 55-60° C. To the residue is added n-heptane and stirred for 1 hour at 25-30° C. The material, is filtered washed with n-heptane (100 ml) and then the material is dried at 50° C. under vacuum to obtain 65 gm of 4-Chloro-6,7-bis-(2-methoxyethoxy)-quinazoline.

Reference Example 2

Step-I

4-Chloro-6,7-bis-(2-methoxyethoxy)-quinazoline (63 gm) and isopropyl alcohol (990 ml) are added to 3-ethynylaniline (23.6 gm) at 25-30° C. while stirred, the contents are heated to reflux and then refluxed for 1 hour 30 minutes to 2 hours. The reaction mass is cooled to 25-30° C. and stirred for 30 minutes. The material, is filtered, washed with chilled isopropyl alcohol (400 ml) followed by n-hexane (300 ml) and then the material is dried at 50-60° C. under vacuum for 6 hours to give 75 gm of crude erlotinib hydrochloride [HPLC purity: 97%; Content of N-methoxyethyl impurity: 0.24% (at 1.14 RRT)].

Step-II

Crude erlotinib hydrochloride (37 gm, obtained in step-I), water (370 ml) and chloroform (370 ml) are taken into a reaction flask at 25-30° C. and stirring begun. The contents are heated to 50-55° C., sodium hydroxide solution is added at 50-55° C. and then stirred for 15 minutes at 50° C. (clear solution not observed). To the reaction mass is added chloroform (200 ml) and methanol (60 ml) and stirred for 15 minutes at 50° C. (clear solution observed). The layers are separated at 50° C., the organic layer is washed with water (200 ml) at 50° C. and then the organic layers are combined. To the organic layer is added methanol (60 ml) and then dried over sodium sulfate and the total solvent is distilled under vacuum at 50-55° C. To the residue is added n-heptane (300 ml) and stirred for 30 minutes at 25-30° C. The material, is filtered washed with n-heptane (70 ml) and then the material is dried at 60-65° C. under vacuum for 3 hours 30 minutes to give 34 gm of erlotinib free base [HPLC purity: 98.2%; Content of N-methoxyethyl impurity: 0.24% (at 1.14 RRT)].

Step-III

Erlotinib free base (5 gm, obtained in step-II) is dissolved in chloroform (200 ml) at 25-30° C. to form a clear solution and then is added diethyl ether (50 ml). To the resulting solution is slowly added 15% diethyl ether HCl (5 ml) at 25-30° C. and stirred for 30 minutes at 25-30° C. The material, is filtered washed with a mixture of diethyl ether (10 ml) and chloroform (10 ml), and then dried at 60-65° C. under vacuum to give 4.9 gm of erlotinib hydrochloride [HPLC purity: 99.7%; Content of N-methoxyethyl impurity: 0.24% (at 1.14 RRT)].

EXAMPLES

Example 1

4-Chloro-6,7-bis-(2-methoxyethoxy)-quinazoline (50 gm) and dimethyl sulfoxide (250 ml) are added to methanol (500 ml) while stirred at 25-30° C., 3-ethynylaniline (20.5 gm) is added to the reaction mixture at 25-30° C. and then the contents are heated to 85° C. The reaction mass is stirred for 2 hours at 80-85° C., the mass is cooled to 25-30° C. and then stirred for 1 hour. The material is filtered, washed with a mixture of dimethyl sulfoxide (50 ml) and methanol (100 ml), and then dried at 60° C. under vacuum for 4 hours to give 60 gm of erlotinib hydrochloride [HPLC purity: 99.65%; Content of N-methoxyethyl impurity: 0.09% (at 1.14 RRT)].

Example 2

Crude erlotinib free base (10 gm, HPLC purity: 98.2%; Content of N-methoxyethyl impurity: 0.24%) is dissolved in dimethylsulfoxide (50 ml) at 25-30° C., to the solution is added 15% methanolic HCl (100 ml) at 25-30° C. while the pH of the mass is adjusted to 2 and then stirred for 30-40 minutes at 25-30° C. The material is filtered, washed with a mixture of dimethyl sulfoxide (10 ml) and methanol (20 ml), and then the material is dried at 60-65° C. under vacuum for 5 hours to give 8.9 gm of pure erlotinib hydrochloride [HPLC purity: 99.92%; Content of N-methoxyethyl impurity: 0.02% (at 1.14 RRT)].

Example 3

Crude erlotinib hydrochloride (20 gm, HPLC purity: 99.7%; Content of N-methoxyethyl impurity: 0.24%) is suspended in dimethylsulfoxide (225 ml) at 25-30° C. and heated to 65-70° C. (clear solution not observed). To the suspension is added methanol (475 ml) at 65-70° C. and stirred for 30 minutes at 70° C. to form a clear solution, the solution is gradually cooled to 20° C. and then stirred for 1 hour at 20-25° C. The material is filtered, washed with a mixture of dimethyl sulfoxide (10 ml) and methanol (20 ml), and then the material is dried at 60-65° C. under vacuum for 5 hours to give 16.8 gm of pure erlotinib hydrochloride (HPLC purity: 99.95%; Content of N-methoxyethyl impurity: Not detected).

Without further elaboration of the foregoing will so fully illustrate our invention that others may, by applying current or future knowledge, adapt the same for use under various conditions of service

We claim:

1. A process for the preparation of erlotinib or a pharmaceutically acceptable salt thereof substantially free of N-methoxyethyl impurity, wherein the N-methoxyethyl impurity is N-[(3-ethynylphenyl)-(2-methoxyethyl)]-6,7-bis (2-methoxyethoxy)-4-quinazolinamine, comprising
    dissolving crude erlotinib or a crude pharmaceutically acceptable salt of erlotinib in a solvent medium comprising dimethyl sulfoxide and an alcoholic solvent;
    isolating erlotinib substantially free of N-methoxyethyl impurity from the solvent medium, wherein the erlotinib substantially free of N-methoxyethyl impurity has less than 0.1 wt % of N-methoxyethyl impurity.

2. The process as claimed in claim 1, wherein the alcoholic solvent is methanol, ethanol, isopropanol, tert-butanol, amyl alcohol, isoamyl alcohol, tert-amyl alcohol, or a mixture thereof.

3. The process as claimed in claim 2, wherein the alcoholic solvent is methanol or ethanol.

4. The process as claimed in claim 3, wherein the alcoholic solvent is methanol.

5. The process as claimed in claim 1, wherein the pharmaceutically acceptable add addition salts of erlotinib are obtained from hydrochloric acid, hydrobromic acid, hydroiodic acid, methanesulfonic acid or benzenesulfonic acid.

6. The process as claimed in claim 5, wherein the pharmaceutically acceptable acid addition salt of erlotinib is erlotinib hydrochloride.

7. A process for the preparation of erlotinib or a pharmaceutically acceptable salt thereof substantially free of N-methoxyethyl impurity, wherein the N-methoxyethyl impurity is N-[(3-ethynylphenyl)-(2-methoxyethyl)]-6,7-bis(2-methoxyethoxy)-4-quinazolinamine, comprising
  a) reacting 4-chloro-6,7-bis-(2-methoxyethoxy)-quinazoline with 3-ethynylaniline or its hydrochloride salt in a solvent medium comprising dimethylsulfoxide and an alcoholic solvent in the presence or absence of a base; and
  b) isolating erlotinib as free base or a pharmaceutically acceptable acid addition salt substantially free of N-methoxyethyl impurity, wherein the erlotinib substantially free of N-methoxyethyl impurity has less than 0.1 wt % of N-methoxyethyl impurity.

8. The process as claimed in claim 7, wherein the reaction in step (a) is carried out between about 60° C. and reflux temperature of the solvent medium used.

9. The process as claimed in claim 8, wherein the reaction is carried out between about 65° C. and reflux temperature of the solvent medium used.

10. The process as claimed in claim 9, wherein the reaction is carried out between about 70° C. and reflux temperature of the solvent medium used.

11. The process as claimed in claim 7, wherein the reaction in step (a) is carried out in the absence of a base.

12. The process as claimed in claim 7, wherein the pharmaceutically acceptable acid addition salts of erlotinib are obtained from hydrochloric acid, hydrobromic acid, hydroiodic acid, methanesulfonic acid or benzenesulfonic acid.

13. The process as claimed in claim 12, wherein the pharmaceutically acceptable acid addition salt of erlotinib is erlotinib hydrochloride.

14. The process as claimed in claim 1, wherein isolating erlotinib substantially free of N-methoxyethyl impurity from the solvent medium comprises, adding an acid to the solution, and collecting the precipitated solid to obtain an erlotinib pharmaceutically acceptable acid addition salt substantially free of N-methoxyethyl impurity.

15. The process as claimed in claim 14, wherein the acid used is an organic or inorganic acid.

16. The process as claimed in claim 15, wherein the acid is selected from hydrochloric acid, hydrobromic acid, hydroiodic acid, methanesulfonic acid and benzenesulfonic acid.

17. The process as claimed in claim 16, wherein the acid is hydrochloric acid.

18. The process as claimed in claim 17, wherein the hydrochloric acid is used in the form of aqueous hydrochloric acid or in the form of hydrogen chloride gas or hydrogen chloride dissolved in an organic solvent.

19. The process as claimed in claim 18, wherein the organic solvent used for dissolving hydrogen chloride gas or hydrogen chloride is selected from the group consisting of ethanol, methanol, isopropyl alcohol, ethyl acetate, diethyl ether, dimethyl ether and acetone.

20. The process as claimed in claim 14, wherein the precipitated erlotinib pharmaceutically acceptable acid addition salt substantially free of N-methoxyethyl impurity is collected by filtration or centrifugation.

21. The process as claimed in claim 1, wherein the crude erlotinib is a pharmaceutically acceptable acid addition salt and the process includes isolating the pharmaceutically acceptable acid addition salt substantially free of N-methoxyethyl impurity.

22. The process as claimed in claim 21, wherein isolating is carried, out by cooling, partial removal of the solvent from the solution, addition of precipitating solvent or a combination thereof.

23. The process as claimed in claim 1, wherein the erlotinib or a pharmaceutically acceptable salt of erlotinib contains the N-methoxyethyl impurity in less than about 0.05% by weight.

24. The process as claimed in claim 23, wherein the erlotinib or a pharmaceutically acceptable salt of erlotinib contains no traces of the N-methoxyethyl impurity as measured by HPLC.

* * * * *